United States Patent [19]

Romberg et al.

[11] Patent Number: 4,973,504

[45] Date of Patent: * Nov. 27, 1990

[54] PHARMACEUTICAL ELASTOMERIC COATING

[75] Inventors: Val G. Romberg, Parkerford; Patty H. Kiang, Collegeville; Wayne T. Curry, Pottstown, all of Pa.

[73] Assignee: The West Company Incorporated, Phoenixville, Pa.

[*] Notice: The portion of the term of this patent subsequent to Feb. 28, 2006 has been disclaimed.

[21] Appl. No.: 267,828

[22] Filed: Nov. 7, 1988

Related U.S. Application Data

[63] Continuation-in-part of Ser. No. 37,959, Apr. 13, 1987, Pat. No. 4,808,453.

[51] Int. Cl.$^5$ ............................................. B65D 81/24
[52] U.S. Cl. ............................ 428/36.8; 428/494; 428/495; 428/519; 428/521; 215/364; 220/DIG. 19; 528/396
[58] Field of Search ......... 215/364; 220/19, DIG. 19; 428/36.8, 494, 495, 519, 521; 528/396

[56] References Cited

U.S. PATENT DOCUMENTS

| | | | |
|---|---|---|---|
| 3,288,728 | 11/1966 | Gorham et al. | 528/125 |
| 3,300,332 | 1/1967 | Gorham et al. | 428/403 |
| 3,342,754 | 9/1967 | Gorham et al. | 428/195 |
| 3,927,695 | 12/1975 | Crockwell | 138/137 |
| 4,082,862 | 4/1978 | Esemplare et al. | 428/494 |
| 4,808,453 | 2/1989 | Romberg et al. | 428/36.8 |

Primary Examiner—George F. Lesmes
Assistant Examiner—Christopher Brown
Attorney, Agent, or Firm—Eugene E. Renz, Jr.

[57] ABSTRACT

An elastomeric member for use with a container and in contact with pharmaceutically pure contents therein. The elastomeric member has an elastomeric base and a continuous polyparaxylylene coating on the base. The coating ranges from about 0.5 microns to about 2.0 microns in thickness. The closure member has a coefficient of friction of less than 1.0 and is capable of substantially preventing metal extraction from said elastomers.

8 Claims, 2 Drawing Sheets

PHARMACEUTICAL ELASTOMERIC COATING

FIELD OF THE INVENTION

This invention relates to pharmaceutical products which includes a container having pharmaceutically pure contents and an elastomeric member which is also in contact with the contents. The elastomeric member has an elastomeric base and a continuous poly (p-xylylene) coating of from about 0.5 microns to 2 microns in thickness.

BACKGROUND OF THE INVENTION

For many years, the most successful closure system for pharmaceutical products has been the use of elastomeric members in glass or plastic vials. The glass and rubber combination has been useful for a wide variety of pharmaceutical ingredients combining both safe storage of the medicine and easy access through the rubber stopper. Particularly, when liquids are contained in the vial, a needle can easily penetrate the rubber to withdraw the desired amount of ingredient without otherwise interfering with the integrity of the closure. Even when powders are stored in such containers, the elastomeric member can be penetrated with a needle to activate the powder by adding liquid such as pure water. The activated medicine remains in a safe, protected environment.

Because of the success of these types of pharmaceutical devices, and as more and more systems have been using rubber in combination with glass containers, the rate at which these devices can be manufactured contributes greatly to the economic efficiencies of this otherwise desirable component design. For example, conventional pharmaceutical devices which are useful for filling vials rely on a mechanical implantation of the rubber stopper into the neck of the vial or other shaped container. Just prior to the mechanical insertion, the rubber stoppers are transported from a hopper to the stoppering equipment, usually by centrifugal, vibrating or gravity feed. It is essential that the rubber components not hang up on each other or on the transfer equipment. It is essential that they flow smoothly into the capping or closure-forming device. The equipment, particularly that for transferring components, is normally made from stainless steel or other materials which can be kept extremely clean for pharmaceutical purposes. The ability of the rubber component to slide smoothly on the surface is directly dependent upon its coefficient of friction, with the lower values for coefficient of friction being far more desirable. Also, it is important that the elastomeric components do not stick to one another during travel through this transfer equipment.

In the prior art, the high coefficient of friction of rubber stoppers and other rubber materials which are being fed to closure devices and other pharmaceutical devices has been the limiting factor in the speed of the machine. Whether gravity of centrifugal force or vibration feeding devices are used, they require that the rubber stoppers or other elastomeric components move smoothly over the surface of the feeding unit as rapidly as possible. Typically, rubber devices of the type used in pharmaceutical closures have coefficients of friction of at least 1.2. This clearly acts as an impediment to rapid movement and, therefore, efficient and low cost production.

One solution which has been proposed to improve the general processibility of rubber closures and which has at least kept the individual rubber stoppers from binding to one another during autoclaving and other treating steps, is the use of silicone oil as a coating on the outside of the stoppers. Silicone oil has improved the lubricity of the rubber closures but has also added additional problems. The use of silicone oil increases the particle count found during the inspection of various drug solutions. The Food and Drug Administration evaluates processes by counting the number of particles present, without concern for the source or nature of the particles. Silicone oil in small amounts, is normally not an undesirable contaminant in medicine but its use still adds to the count of particles and, therefore, detracts from the overall acceptance of its use in processing equipment. While the amount of silicone oil is minimal, being only that amount necessary to prevent the individual stoppers from sticking to one another, silicone oil is not able to adequately lower the coefficient of friction of rubber stoppers for use in high speed capping equipment so as to give uniform faster movement, particularly with centrifugal feeding systems. Finally, the rubber stoppers which have been treated by the use of silicone oil are not any more effective in surviving chemical tests concerning the compatibility with and contamination of material contained in the vials. Similarly, in plunger tips for syringes, the need for silicone lubricant to reduce break loose and extrusion forces required for operation is another area of significant silicone contamination which has been necessary to this time.

The elastomeric materials which are used in the pharmaceutical industry are carefully selected and formulated to be as inert as possible when in contact with pharmaceutical products such as medicines and the like. Formulations and products are checked constantly to determine that they are not being contaminated. Of particular importance in addition to the above-mentioned particle count produced by silicone oil are particles which come off of the elastomeric closure itself. Additionally, certain trace metals are employed in the manufacture of elastomeric compounds in many instances, and it is essential that these materials not be extracted to any significant extent by the medicines or other pharmaceutical fluids which are in contact with the elastomeric products. Of particular concern are metals such as calcium, aluminum and heavy metals such as zinc and lead. Accelerated and ultra-vigorous tests are used to determine the amount of these undesirable materials which potentially may be extracted from elastomeric materials. If the quantity of extractable metals produced when products are subjected to vigorous testing is not beyond the level produced under normal conditions, the medicine would be free from likely contamination.

At the present time, pharmaceutical products have not been manufactured using a container having pharmaceutically pure contents therein and an elastomeric closure member closing said container, wherein the elastomeric closure member has an elastomeric base and a coating over the elastomeric base which substantially improves the coefficient of friction and significantly reduces the amount of extractable metal ions which are potentially extractable from the elastomeric closure member. A variety of materials have been proposed as coating materials for a variety of other purposes generally. However, coating the entire surface of elastomeric closure members such as rubber stoppers for use with containers having pharmaceutically pure contents therein has not become an accepted practice in the pharmaceutical industry wherein the objects would be satisfied. It is particularly undesirable to coat a pharmaceutical product with a material which alters the physical characteristics of the elastomer, such as by increasing stiffness on "feel".

One material which has been found to be extremely useful as a coating material generally are the polymers of the various paraxylylenes. Gorham U.S. Pat. No. 3,288,728 discloses a basic method of preparing linear copolymers from paraxylylenes using temperature conditions between 450° C. and 700° C. This patent suggests that small articles can be protected or encapsulated with these polymers to obtain the insulative and protective properties of the polyparaxylylenes. The reference generally suggests that there are enumerable possible applications for the polymer as a coating material.

Gorham U.S. Pat. No. 3,342,754 describes the broad method of preparing linear polymers of paraxylylene and particularly in preparing coatings using that material. The patent is replete with a variety of examples of variations and suggests that these polymers are desirable for use as a film, fiber, surface coating, or electrical insulation. Both this patent and the previous Gorham patent, offers the general suggestion that almost any material may be coated with the paraxylylene polymers, although neither has a specific example relating to the pharmaceutical industry.

Tittman et al U.S. Pat. No. 3,379,803 describes particular apparatus and methods useful for polymerizing paraxylylene. General disclosures using this material indicating that a continuous film may be prepared on a wide variety of substrates. Tittman et al's related U.S. Pat. No. 3,472,795 describes an additional method for increasing the coating thickness.

Parent U.S. Pat. No. 4,225,647 discloses a process for coating an extremely broad list of materials with polymers of paraxylylene. The coating of articles may range from less than 50 Angstroms to as thick as 5 mils or more. The Parent patent suggests that a first layer of substituted silicon compounds be employed prior to the polyparaxylylene coating.

Finally, Gorham et al U.S. Pat. No. 3,300,332 describes a coating process wherein the object is to coat with an insoluble coating. The thickness of the coating is not described in detail but Gorham suggests that the thickness of the polymeric coating is not narrowly critical but is dictated by the end use of the product. He describes a coating of 0.1 mil as being very thin and useful when desiring resistance to solvent or reactive attack. In one Example, six rubber stoppers are coated to protect them from swelling from solvents such as heptane. The amount of coating added ranges from 0.22 to 0.28 grams, indicating a thickness of at least 1 mil. There is, of course, no indication that the coefficient of friction or the resistance to extraction by various means of metals could be accomplished so as to provide a superior product for use with pharmaceuticals. Tests have been run which clearly demonstrate that stoppers of the Gorham et al patent are totally non-functional as stoppers, for example. In one test, 4 out of 10 stoppers were unable to seal at all. Needle penetration increased by over 80%, based upon an uncoated stopper.

In most cases, pharmaceutical elastomers must be selected with extreme care to prevent metals and organics from being extracted. Turbidity is also a problem which requires special procedures and material selection for elastomers.

When elastomers are selected for baby bottle nipples, a particular concern arises in that infant feeding is extremely sensitive to texture and softness of the product. Therefore, any coating such as that of Gorham et al which materially alters the physical nature of the bottle nipple is totally undesirable. In this particular health care product, efforts to improve the product texture and softness have caused an increase in the quantity of elastomers being used, as softness and strength are conflicting attributes.

SUMMARY OF THE INVENTION

Accordingly, it has now been discovered that an improved pharmaceutical product may be prepared for use in the following manner. The product comprises a container with a pharmaceutically pure contents therein and an elastomeric member closing said container. The elastomeric member has an elastomeric base and a continuous polyparaxylylene coating of from about 0.5 microns to about 2 microns on the elastomeric closure. The coating is sufficient to reduce the coefficient of friction of the closure member to less than 1.0 and preferably less than about 0.5. The coating is also sufficient to substantially prevent metal ion extraction from the elastomer. Particularly, the coating acts to prevent metal ion extraction so that from 50 to 1000 fold less metal ions are extracted in one hour when autoclaving in 1 molar hydrochloric acid. Also, substantial reduction or elimination of organic extractables is achieved by the use of the present invention. In the baby bottle nipple, the tensile strength of an uncoated base increased without increasing the hardness of the elastomer.

It has been found that the narrow range of about 0.5 microns to about 2.0 microns is particularly suited for preparation of coatings on elastomeric members. The coating substantially improves the economics of manufacturing pharmaceutical products because of the significant improvement in coefficient of friction, thereby allowing the production of finished products at much higher rates. At the same time, the amount of coating employed is significantly less than what one would expect in accomplishing the barrier properties which are necessary for this process, thereby significantly reducing the cost contribution of the polyparaxylylene which is employed.

BRIEF DESCRIPTION OF THE DRAWINGS

These and other objects of the present invention and the various features and details of the operation and construction thereof are hereinafter more fully set forth with reference to the accompanying drawings, where.

DETAILED DESCRIPTION OF THE PREFERRED EMBODIMENT

Figure 1:
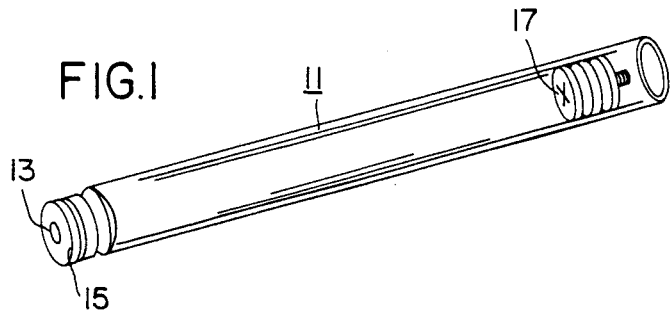
FIG. 1 shows a perspective view of a syringe cartridge and plunger.

The devices of this invention may be manufactured from any conventional elastomeric base material which has been used in pharmaceutical devices where an elastomeric component is required. Such materials are formed into rubber stoppers, plunger tips, pre-filled syringes, sleeve stoppers, flashback bulbs, caps, liners, washers, and other elastomeric members which are in contact with the contents of a container in which there is a pharmaceutically pure material. Also included are baby bottle nipples.

The combination of an elastomeric closure with the polyparaxylylene coating should be sufficient to reduce the coefficient of friction to less than 1.0 and preferably to about 0.5 or less so that high-speed capping and filling equipment may be used to give uniform and rapid movement of the materials, particularly when a centrifugal feed is employed. This coating allows for the elimination of silicone oil in processing, thereby substantially reducing the particles which may be found in the solution which ultimately comes in contact with the elastomeric closure.

The elastomeric component of the pharmaceutical devices described therein may be manufactured from many of the elastomeric compounds which have conventionally been used in the pharmaceutical industry. Natural rubber, of course, was the original choice of materials for many elastomeric formulations and components in the pharmaceutical industry. Butyl rubber and many of the synthetic elastomers have been successfully used as stoppers, plunger tips, and the like, depending upon the requirements for stability during autoclaving or sterilization. A particular rubber which is admirably suited for the purposes of this invention is butyl rubber.

The present invention is intended to be used on all of the conventional preexisting stoppers and other elastomeric articles which are available in the pharmaceutical industry. Accordingly, any elastomeric base which has been used or which would be usable if the coefficient of friction and barrier to metal extraction are adequate, is therefore contemplated for use as the first component of the present invention. With baby bottle nipples and other products which have a special texture and softness, it is also necessary to preserve the feel of the product.

Presently available rubber products are admirably suited for their purpose in the pharmaceutical industry, except for the delay caused in high-speed machines and the potential for extraction of metal ions. Accordingly, the present invention seeks to improve the stopper's functionality in these areas while maintaining its functionality in all of the remaining areas. Specifically, the invention contemplates improving the coefficient of friction of the closure member for use in high-speed capping equipment, particularly with centrifugal feeds. It also contemplates the elimination of silicone oil and other processing aids. Also, the invention contemplates the significant improvement in resisting extraction of metal ions from rubber products which are otherwise suited for use in the pharmaceutical industry. Also, some elastomers contain organic extractables. The effectiveness of the rubber materials as a barrier and as a stopper and as a product resistant to chemical attack is intended to be maintained when this second component is applied. Because elastomeric members currently in use are admirably suited except for the above-mentioned deficiencies, there is no significant reason for improving any of these other properties. Nonetheless, it is necessary to maintain these properties when applying the coating as described hereinafter. In baby bottle nipples, it is desired to increase tensile strength while decreasing softness or to permit the use of softer elastomeric formulations by increasing tensile strength and preserving all of the remaining properties.

Polymers made from the various paraxylylenes may be applied as a coating in the manner which has been described previously in the various patents discussed hereinabove. Specifically, as an example of various paraxylylene polymers and paraxylylene copolymers, the previously referenced Gorham U.S. Pat. Nos. 3,342,754 and 3,288,728 describe the chemistry of the polymers and copolymers which may be employed as coatings in the present invention. The Tittman et al U.S. Pat. Nos. 3,379,803 and 3,472,795 describe suitable methods for applying these particular polymers and copolymers onto a wide variety of materials. It has been found that these processes generally are suitable for applying polymers and copolymers of paraxylylene to the elastomeric base materials contemplated in the present invention. The term polyparaxylylene is intended to include both polymers and copolymers of the various paraxylylenes which are described in the prior art.

Figure 2:
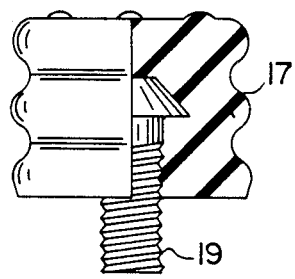
FIG. 2 shows an enlarged view of the plunger shown in FIG. 1.

As shown in the drawings, a variety of elastomeric products may be coated to demonstrate the efficacy of the present invention. In FIG. 1, a cartridge syringe 11 includes both an end seal 13 with a metal cap 15 and an insert plunger 17. Both seal 13 and plunger 17 are coated with the paraxylylene coatings of this invention. In FIG. 2, the plunger 17 is shown in greater detail with the threaded stud 19 for attachment to a syringe plunger.

Figure 3:
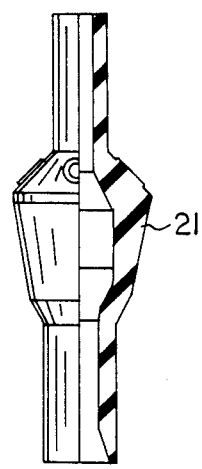
FIG. 3 is a perspective view of a flashback bulb.
Figure 4:
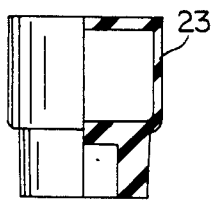
FIG. 4 is a perspective view of a sleeve stopper.
Figure 5:
FIG. 5 is a perspective view of an elastomeric cap.

In FIG. 3, a flashback bulb 21 used in intravenous feeding bottles and related equipment is shown, while sleeve stopper 23 and cap 25 are illustrated in FIG. 4 and FIG. 5 respectively.

Figures 6, 7:
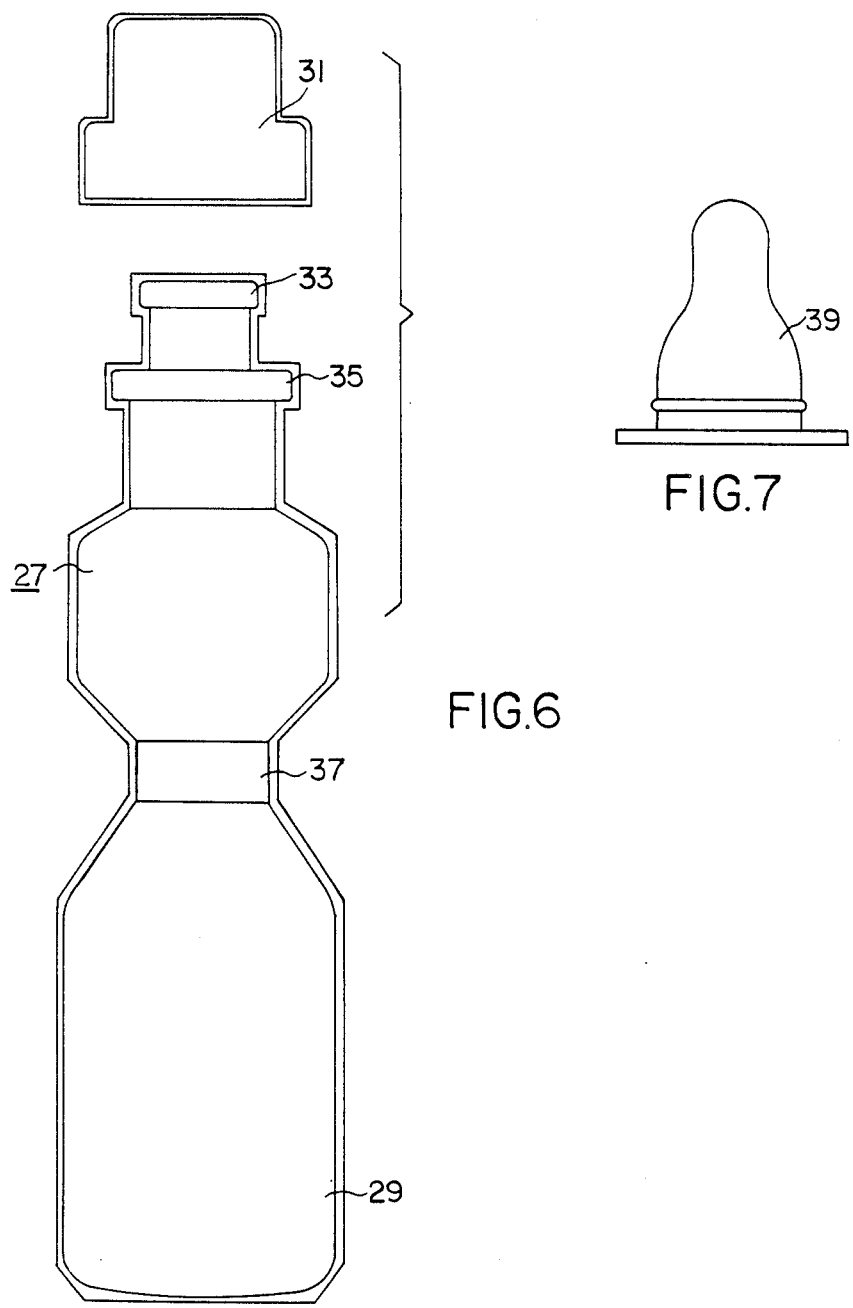
FIG. 6 is a perspective view of a combination two-compartment vial package with an elastomer top plunger and an elastomer center seal.
FIG. 7 is a perspective view of a baby bottle nipple.

FIG. 6 shows a two-compartment vial package with upper bottle 27 and lower bottle 29. Upper bottle 27 has a dust cap 31, rubber top plunger 33 and aluminum ferrule 35. Lower vial 29 has a rubber center seal 37.

FIG. 7 shows a baby bottle nipple 39 which has improved tensile strength because of a coating as described herein. This permits the use of a softer or thinner elastomeric base.

The coatings applied to the elastomeric base members of the present invention produce a product which has a superior coefficient of friction. For the purposes of this invention, the coefficient of friction is defined as follows: the coefficient of friction is the ratio of frictional forces resisting movement of the surface being tested to the force applied normal to the surface. In this case, the surface used was a stainless steel plate. Rubber stoppers and other products tested in these experiments were fixtured in a 256 gram weight such that all of them lie on the stainless steel plane. The incline of the plane was then increased until the weight commenced to slide, at which point the plane was locked and the angle was noted. The tangent of the angle is the static coefficient of friction.

It has been found that the paraxylylene polymer coatings on elastomeric bases improves the coefficient of friction from in excess of 1.5 to less than 1.0 and often times to less than about 0.5.

In order to demonstrate the efficacy of the present invention, the following experiments were performed. In each case, the conventional rubber stopper used in the variety of applications in the pharmaceutical industry was employed. A particular elastomer was a butyl rubber and is generally known in the trade as a 4416/50 gray S-127 pharmaceutical stopper. The rubber stoppers were coated with polychloroparaxylylene in the manner described above, at a thickness ranging from less than 0.5 microns to more than 2.0 microns. The results in each case represent an average of a number of stoppers.

Presented below in Table I are the results of various tests for coefficient of friction measured as described above.

TABLE I

Coefficient of Friction Measurement

| Elastomeric Closure Member | Coefficient of Friction (tangent of the angle of slide) |
| --- | --- |
| Uncoated | 1.7 |
| Silicone coated | 1.0 |
| 0.1 microns polychloroparaxylylene | 1.0 |
| 0.5 microns polychloroparaxylylene | 0.5 |
| 1.0 microns polychloroparaxylylene | 0.18 |
| 2.0 microns polychloroparaxylylene | 0.10 |

Another series of experiments were performed to compare uncoated rubber products such as elastomer seals, caps and the like with those coated with a polyparaxylylene coating of a thickness of 1.0 microns. The tests performed were the standard U.S. Pharmacopic-National Formulary Testing and the results are presented below in Table II.

TABLE II

Standard USP-NF Testing

| Test | Uncoated | 1.0 Micron Coating of Polychloroparaxylylene |
| --- | --- | --- |
| pH shift | −0.8 | −0.4 |
| Nephelos (turbidity) | 12 | 1 |
| Reducing substances (MLS-$I_2$) | 0.0 | 0.0 |
| Total solids (MGS) | 1.2 | 0.4 |
| UV | No absorbence | No absorbence |

As can be seen from a comparison of the data in Table II, the elastomeric member in combination with the polyparaxylylene coating is substantially superior to the uncoated rubber product. All of the values for the uncoated material are acceptable by pharmaceutical industry standards, but the improved results demonstrate that the present invention does not adversely affect the acceptability of the product, but rather enhances the acceptability.

In order to measure the potential for extraction of metals, a quantity of rubber stoppers, seal caps, center seals for two vial units, and the like were autoclaved at 120° C. in 100 ml of 1 molar hydrochloric acid for 1 hour. The acid was then analyzed by atomic absorption analysis for both a zinc and aluminum concentration. Presented below in Table III are the results of uncoated rubber products and rubber products coated with 2 microns of polychloroparaxylylene. The improvement ranges from 35 to nearly 1000 fold improvement.

TABLE III

| Extractable Metal | Uncoated | Coated (2 microns) |
| --- | --- | --- |
| Aluminum (ppm) | 7.0 | 0.2 |
| Zinc (ppm) | 94.0 | 0.1 |

Other tests were run to determine the effect of coating thickness on extractable metals of a different rubber, 817 gray, which can be used for a variety of products. The tests were performed and the results are shown below in Table IV. In this series of tests, the rubber base was autoclaved for 1 hour in 1 molar hydrochloric acid and the acids were then analyzed by atomic absorption analysis for the various metals. Again, it will be noted the surprising results attained by the present invention.

TABLE IV

Thickness Effect of Extractable Metals on 817 Gray Rubber

| Coating Thickness (microns) | Calcium (ppm) | Aluminum (ppm) | Zinc (ppm) |
| --- | --- | --- | --- |
| 0.0 | 0.17 | 4.2 | 50 |
| 0.1 | 0.15 | 1.8 | 35 |
| 0.5 | 0.03 | 0.1 | 12 |
| 1.0 | <0.002 | <0.05 | 0.2 |
| 2.0 | <0.002 | <0.05 | <0.05 |

Even though the prior art indicates coatings generally are possible at thicknesses of about 0.1 mil, or 2.5 microns, the surprising effectiveness of the narrow range of this invention dramatically demonstrates the superiority of this coated elastomer in a pharmaceutically critical environment, wherein an improvement of from 50 to 1000 is observed.

The effect of the polyparaxylylene coating on various rubber products was also measured for other properties which pharmaceutical products are required to have. In one series of tests, coring was measured using a 20 gauge reusable needle with 10 punctures in each stopper. A new needle was used for each 40 punctures. The contents of the vials were then examined on a black filter and no coating flakes were found. Coated and uncoated rubber were then autoclaved at 121° C. for 1 hour in steam and water. The uncoated stoppers were tacky and stuck together in each case. Coated stoppers were free flowing and non-tacky and no damage to the coating was observed.

Coated and uncoated stoppers were tested for needle penetration using double-ended 21 gauge disposable needles. A penetration speed of 5 in/min was used. The force required for both coated and uncoated rubber stoppers was substantially the same in both cases.

Tests were also performed which demonstrates that the amount of extractable organic was very substantially reduced, if not eliminated.

One test used to determine the amount of particulates clearly demonstrates the improved results that polyparaxylylene coatings on stoppers provide when compared to the stoppers which have been treated with silicone to increase the flowability of the products through a centrifugal feeding apparatus during the closure step. Coated, uncoated and silicone treated stoppers were placed in 150 ml of filtered deionized water. These were then mixed for 30 minutes and the particles in a 10 ml sample were counted. Particles greater than or equal to 5 microns were counted and calculated. Both coated and uncoated stoppers had less than 300 particles per stopper, while those which were treated with silicone had in excess of 10,000 particles per stopper.

A variety of coatings were applied to rubber stoppers for evaluation during the manufacture of pharmaceutical closures. Specifically, pharmaceutical products which have a container with pharmaceutically pure contents were closed with an elastomeric closure member of the type described herein. These closures included an elastomeric closure having an elastomeric base and a continuous polyparaxylylene coating ranging from about 0.5 microns to about 2.0 microns. The stoppers were first autoclave sterilized at 135° C. for 12 minutes. They were then located into a stoppering machine. These stoppers were unusable in some cases because the autoclaving step caused the stoppers to stick together, causing shutdown of the machine. Next, the products prepared according to the present invention were loaded into the stoppering machine after autoclaving as described above. The maximum speed of the stoppering machine was excellent and successful production was achieved without silicone oil, demonstrating the substantial economies which are achieved using the present invention.

Finally, baby bottle nipples were coated with polyparaxylylene coating and tested. The nipples demonstrated an increase in tensile strength while also keeping the degree of softness desired. For the first time, it was possible to produce a baby bottle nipple that met all four major requirements. The nipples were soft, had good strength, has negligible heavy metal ion extraction and could be sterilized repeatedly without harm.

A variety of pharmaceutical products may be used in the container having the closure of this invention. Specifically, pharmaceutical products containing medical and veterinary drugs, distilled water, solvents containing medicines, syrups, serums and the like are unaffected when packaged with elastomeric closures according to the present invention.

What is claimed is:

1. An elastomeric member for use with a container and in contact with pharmaceutically pure contents therein, comprising an elastomeric base and continuous polyparaxylylene coating on said base to reduce the coefficient of friction of said member to less than 1.0 and substantially prevent metal ion extractions from said base, said coating ranging from about 0.5 microns to about 2.0 microns in thickness.

2. The product of claim 1, wherein said coefficient of friction is less than 0.5.

3. The product of claim 1, wherein said extraction is at least 50 fold less calcium ion at 1 hour of autoclaving in 1 molar hydrochloric acid than an uncoated member.

4. The product of claim 1, wherein said extraction is at least 50 fold less aluminum in 1 hour of autoclaving in 1 molar hydrochloric acid than an uncoated member.

5. The product of claim 1, wherein said extraction is at least 50 fold less zinc at 1 hour of autoclaving in 1 molar hydrochloric acid than an uncoated member.

6. The product of claim 1, which further includes a container with pharmaceutically pure contents therein.

7. The product of claim 1, wherein said member is selected from plunger tips, sleeve stoppers, seals, flashback bulbs tops or baby bottle nipples.

8. A baby bottle nipple formed from an elastomeric member, comprising an elastomeric base and a continuous polyparaxylylene coating on said base to substantially prevent metal ion extraction from said base, said coating increasing the tensile strength over an uncoated base without increasing the hardness, said coating ranging from about 0.5 microns to about 2.0 microns in thickness.

* * * * *